(12) United States Patent
Philippe et al.

(10) Patent No.: US 6,562,789 B2
(45) Date of Patent: *May 13, 2003

(54) HISTIDINE DERIVATIVES, PREPARATION PROCESS, AND THEIR USE AS FREE ANTIRADICAL AGENTS

(75) Inventors: Michel Philippe, Wissous (FR); Thierry Bordier, Tremblay en France (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/852,741

(22) Filed: May 11, 2001

(65) Prior Publication Data

US 2002/0165165 A9 Nov. 7, 2002

Related U.S. Application Data

(63) Continuation of application No. 09/319,170, filed as application No. PCT/FR97/01957 on Oct. 31, 1997, now Pat. No. 6,255,344.

(30) Foreign Application Priority Data

Dec. 4, 1996 (FR) ............................................. 96 14880

(51) Int. Cl.$^7$ ..................... A61K 7/00; A61K 38/05; C07K 5/02; C07K 5/023; C07K 5/062
(52) U.S. Cl. ..................... 514/19; 424/401; 548/338.1
(58) Field of Search ............................ 514/18, 19, 400, 514/556, 844, 944, 947; 424/43, 401, 450, 455, 489; 548/338.1

(56) References Cited

U.S. PATENT DOCUMENTS

| | | | |
|---|---|---|---|
| 5,503,776 A | 4/1996 | Murase et al. | 252/397 |
| 5,508,728 A | 4/1996 | Nagai et al. | 514/400 |
| 6,180,116 B1 * | 1/2001 | Philippe et al. | 424/400 |
| 6,255,344 B1 * | 7/2001 | Philippe et al. | 514/556 |
| 6,358,514 B1 * | 3/2002 | Boussouira et al. | 424/401 |

FOREIGN PATENT DOCUMENTS

| | | |
|---|---|---|
| EP | 0 455 528 | 11/1991 |
| EP | 0 500 332 | 8/1992 |
| FR | 2 496 660 | 6/1982 |
| FR | 2 668 365 | 4/1992 |
| FR | 2 680 373 | 2/1993 |
| WO | WO 90/06102 | 6/1990 |
| WO | WO 92/08685 | 5/1992 |
| WO | WO 92/09298 | 6/1992 |

OTHER PUBLICATIONS

Eric A. Decker et al., "Inhibition of Lipid Oxidation by Carnosine", Journal of the American Oil Chemists' Society, vol. 67, No. 10, Oct. 1990, pp. 650–652.

Francis A. Carey et al., Advanced Organic Chemistry, Third Edition, 1985, p. 372.

Patrick Machy et al., Liposomes in Cell Biology and Pharmacology, INSERM publications, 1987, pp. 1–6.

Helmut Ringsdorf et al., "Molecular Architecture and Function of Polymeric Oriented Systems: Models for the Study of Organization, Surface Recognition, and Dynamics of Biomembranes", Angewandte Chemie, vol. 27, No. 1, 1988, pp. 114–158.

André M. Braun et al., "Applications of singlet oxygen reactions: mechanistic and kinetic investigations", Pure and Applied Chemistry, vol. 62, No. 8, Aug. 1990, pp. 1467–1476.

English language Derwent Abstract of EP 0 455 528, (Nov. 6, 1991).

English language Derwent Abstract of FR 2 496 660, (Jun. 25, 1982).

English language Derwent Abstract of FR 2 668 365, (Apr. 30, 1992).

English language Derwent Abstract of FR 2 680 373, (Feb. 19, 1993).

* cited by examiner

*Primary Examiner*—Jeffrey E. Russel
(74) *Attorney, Agent, or Firm*—Finnegan, Henderson, Farabow, Garrett & Dunner, L.L.P.

(57) ABSTRACT

The invention relates to novel histidine derivatives corresponding to the general formula (I) below:

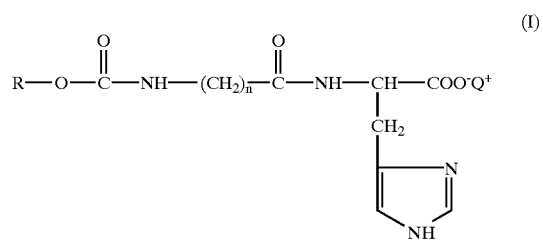

in which:

R denotes a linear or branched, saturated or unsaturated alkyl radical containing from 6 to 22 carbon atoms, n is an integer ranging from 1 to 16, $Q^+$ represents $H^+$ or an organic or inorganic cation, and the addition salts with an acid.

The invention also relates to a process for preparing the compounds of formula (I), as well as to the use of these compounds in cosmetics and pharmacy.

14 Claims, No Drawings

HISTIDINE DERIVATIVES, PREPARATION PROCESS, AND THEIR USE AS FREE ANTIRADICAL AGENTS

This is a continuation of application Ser. No. 09/319,170, filed Jun. 24, 1999, now U.S. Pat. No. 6,255,344, under 35 U.S.C. 371, which is a National Stage of International Application No. PCT/FR97/01957, filed Oct. 31, 1997, incorporated herein by reference.

The present invention relates to novel histidine derivatives and to a process for their preparation. The invention also relates to cosmetic or dermatological compositions comprising these compounds. The invention also relates more particularly to the use of these compounds as anti-free-radical agents.

Solar radiation, heat, atmospheric pollution and, in particular, smoke and tobacco are known to lead to the formation of free radicals. They originate to a large extent from molecular oxygen.

Mention may be made of the following free radicals:
- singlet oxygen, which is highly oxidizing, highly toxic and has a very short lifetime, produced by the excitation of molecular oxygen with photons of light;
- the superoxide anion radical, produced by the addition of an electron to oxygen and capable of giving rise to the production of highly reactive hydroxyl radicals;
- the hydroxyl radical, which is highly oxidizing and the most toxic to cells.

The formation of these radical species leads in particular to oxidation of the lipids in the skin.

Live cells, in particular those in the skin, the scalp and certain mucous membranes, are particularly sensitive to these free radicals, which is reflected in accelerated ageing of the skin, with a complexion lacking radiance and early formation of wrinkles and fine lines, and also by a reduction in the vigour and a dull appearance of the hair.

It is thus seen that it is particularly important to protect the skin, the hair and the mucous membranes against these free radicals.

It is known that certain antioxidants are capable of inhibiting the formation of free radicals.

Thus, carnosine, or N-β-alanyl-L-histidine, which is a natural dipeptide found in the muscles of many vertebrates, is known for its anti-free-radical activity, in particular its activity against singlet oxygen (E. Decker and H. Faraji, JAOCS, vol. 67, No. 10, 650–652, 1990). Its use as an antioxidant or as anti-free-radical agent in cosmetics is also known from patent application WO-A-92/09298. However, when in contact with the skin, carnosine displays degradation problems caused by the enzymes present in the skin and in particular proteases, which leads to a substantial loss of its activity.

Carnosine derivatives are also known, such as, for example, the N-acyl carnosine derivatives described in patent FR-C-2,496,660. Products with antioxidant activity, obtained by coupling fatty acids and carnosine and used in cosmetic preparations, have been described in patent application FR-A-2,668,365. However, such carnosine derivatives also have the same problem of instability in the presence of the enzymes present in the skin.

The Applicant has discovered, unexpectedly, novel histidine derivatives which display greater stability on contact with the enzymes present in the skin, and in particular proteases, than do the known derivatives of the prior art, while at the same time having good anti-free-radical activity and in particular having a good property of efficacy in the deactivation of singlet oxygen. They can thus be used in cosmetics and pharmacy: they are easy to apply to the skin.

The Applicant has found that such results can be obtained with lipodipeptide histidine derivatives containing a carbamate function.

A subject of the invention is thus novel histidine derivatives corresponding to the general formula (I) below:

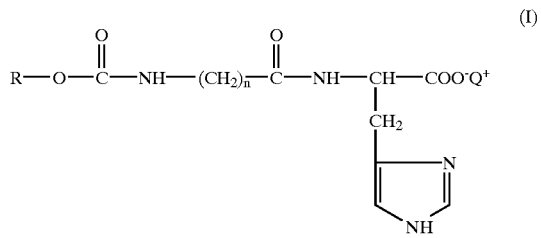

in which:

R denotes a linear or branched, saturated or unsaturated alkyl radical containing from 6 to 22 carbon atoms, n is an integer from 1 to 16, $Q^+$ represents $H^+$ or an organic or inorganic cation, and the addition salts with an acid.

According to the invention, R preferably denotes a linear or branched, saturated alkyl radical containing from 8 to 18 carbon atoms and n is an integer ranging from 1 to 11.

The organic cation can be chosen from ammoniums containing a residue chosen from basic amino acids such as lysine or arginine, or alternatively from amino alcohols such as glucamine, N-methylglucamine or 3-amino-1,2-propanediol.

The inorganic cation can be chosen from alkali metal or alkaline-earth metal cations such as $Na^+$ or $K^+$, or can be the $NH_4^+$ ion.

The addition salts with an acid are chosen, for example, from the hydrochlorides, hydrobromides, sulphates, tartrates and acetates.

The compounds of formula (I) containing an asymmetric carbon in their structure comprise the compounds of D configuration, of L configuration or of D, L configuration.

Among the preferred compounds corresponding to the general formula (I), mention may be made in particular of:
N-octyloxycarbonyl-β-alanyl-L-histidine,
N-dodecyloxycarbonyl-β-alanyl-L-histidine,
N-2-ethylhexyloxycarbonyl-β-alanyl-L-histidine hydrochloride,
N-hexadecyloxycarbonyl-β-alanyl-L-histidine.

A subject of the present invention is also the process for preparing the compounds of formula (I).

This process consists in reacting, in an inert solvent, a compound of formula (II)

X representing a halogen atom, in particular a chlorine atom, or a radical derived from an azole, in particular a radical originating from an imidazole such as that of formula (III):

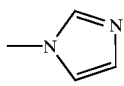
(III)

and R having the same meaning given in formula (I) above,
either (A) with carnosine,
or (B), in a first step, with an amino acid of formula:

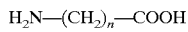
$H_2N-(CH_2)_n-COOH$ to form a compound of formula (IV) below:

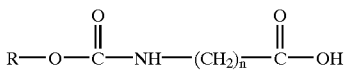
(IV)

$$R-O-\overset{O}{\underset{\|}{C}}-NH-(CH_2)_n-\overset{O}{\underset{\|}{C}}-OH$$

R and n having the same meanings as those given in formula (I) defined above,
and, in a second step, in reacting in histidine with the compound of formula (IV) in the presence of a coupling agent.

The term "coupling agent" refers to any compound capable of substituting the OH group in the compound of formula (IV), and then of being subsequently substituted with histidine. Coupling agents are mentioned in "Advanced Organic Chemistry, J. March, 3rd edition, 1985, page 372". 2-(5-Norbornene-2,3-dicarboximido)-1,1,3,3-tetramethyluronium tetrafluoroborate can be used in particular as a coupling agent.

The starting histidine and carnosine, each containing an asymmetric carbon, are used in the pure optical form or as a mixture (D; L; D,L) depending on the desired optical form of the compound of formula (I)

Dichloromethane, 1,2-dichloroethane, 1,1,1-trichloroethane, chloroform, acetonitrile, toluene, dioxane, tetrahydrofuran, 1,2-dimethoxyethane, cyclohexane, water or a mixture of these solvents can be used as inert solvent.

The reaction is carried out at a temperature preferably between −10° C. and +40° C., and more preferably between 20° C. and 30° C.

The reaction can be carried out in the presence of a base. This can be chosen from alkali metal or alkaline-earth metal hydroxides, sodium hydrogen carbonate, alkali metal alkoxides, alkaline hydrides and tertiary amines such as pyridine or triethylamine. Sodium hydrogen carbonate is preferably used.

The present invention also relates to a composition comprising, in a physiologically acceptable medium, a compound of formula (I) as defined above.

The composition comprising the said compound can be, in particular, in the form of a cosmetic or pharmaceutical composition comprising a cosmetically or pharmaceutically acceptable medium, respectively.

In the compositions according to the invention, the compounds of formula (I) are generally present at a concentration of from 0.01% to 15% by weight, and preferably from 0.1% to 5% by weight, relative to the total weight of the composition.

These compositions can be prepared according to the usual methods known to those skilled in the art. They can be in the form of a lotion, a gel, a water-in-oil or oil-in-water emulsion, a microemulsion, a milk, a cream, a powder, pastes, a solid stick, a spray or an aerosol mousse.

A subject of the invention is also the use of the compounds of formula (I) as anti-free-radical agents, and in particular as anti-free-radical agents for deactivating singlet oxygen, and in particular in a cosmetic or pharmaceutical composition.

The invention also relates to the use of the compounds of formula (I) in a cosmetic or pharmaceutical composition for treating keratin substances against the effects of ageing.

The terms "keratin substances" means the skin, head hair, the nails, other body hairs and mucous and semi-mucous membranes such as the lips.

The Applicant has also discovered, surprisingly, that the compounds of formula (I) constitute anionic amphiphilic lipids which can form stable lipid vesicles.

In a known manner, lipid vesicles are generally characterized by a lipid membrane consisting of substantially concentric leaflets containing one or more multimolecular layers encapsulating a liquid phase. This liquid phase is commonly an aqueous phase. These vesicles are prepared, in a known manner, in the form of a dispersion in an aqueous phase. A non-limiting list of various preparation methods will be found in "Les liposomes en biologie cellulaire et pharmacologie" [Liposomes in cellular biology and pharmacology]—INSERM publications—John Libley, Eurotext, 1987, pages 6 to 18.

A subject of the present invention is thus an aqueous dispersion of lipid vesicles comprising a lipid membrane formed from at least one compound of formula (I) as defined above.

The lipid vesicles in accordance with the invention preferably contain a lipid membrane encapsulating an aqueous phase.

A subject of the present invention is also a cosmetic or pharmaceutical composition containing an aqueous dispersion of lipid vesicles comprising a lipid membrane formed from at least one compound of formula (I).

Another subject of the invention also consists in using the compounds of formula (I) as defined above as amphiphilic lipids capable of forming lipid vesicles.

According to the invention, any ionic and/or nonionic amphiphilic lipid capable of forming stable vesicles, alone or as a mixture with additives whose function is to reduce the permeability of the vesicle membranes and to improve their stability, can be used as a mixture with the compounds of formula (I) to constitute lipid membranes of the vesicles according to the invention. The lipid phase constituting the membranes of the vesicles in the dispersion according to the invention can thus comprise, in a known manner, at least one amphiphilic lipid chosen from the group formed by nonionic amphiphilic lipids and ionic amphiphilic lipids.

The nonionic amphiphilic lipids used with the compounds of formula (I) to form the lipid membrane of the vesicles according to the invention can be chosen from:
(1) the glycerol derivatives of formula:

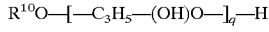
$R^{10}O-[-C_3H_5-(OH)O-]_q-H$ in which:
—$C_3H_5(OH)O$— is represented by the following structures, taken as a mixture or separately:

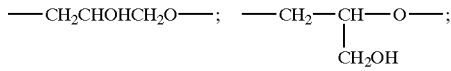
$-CH_2CHOHCH_2O-$; $-CH_2-\underset{CH_2OH}{\overset{|}{CH}}-O-$;

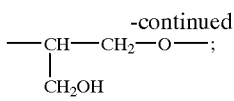

q is an average statistical value between 2 and 6;
$R^{10}$ represents:
(a) a linear or branched aliphatic chain containing from 12 to 18 carbon atoms;
(b) a residue $R^{11}CO$, in which $R^{11}$ is a linear or branched aliphatic $C_{11}$–$C_{17}$ radical;
(c) a residue $R^{12}$—[—$OC_2H_3(R^{13})$—]—, in which:
$R^{12}$ can take the meaning (a) or (b) given for $R^{10}$;
$OC_2H_3(R^{13})$— is represented by the following structures, taken as a mixture or separately:

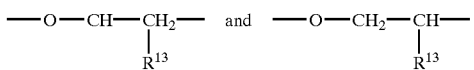

in which $R^{13}$ takes the meaning (a) given for $R^{10}$;
(2) polyoxyethylenated fatty alcohols and polyoxyethylenated sterols,
(3) optionally polyoxyethylenated polyesters;
(4) natural or synthetic glycolipids;
(5) oxyethylenated polyglyceryl stearate;
(6) the glycerol derivatives described in PCT patent application No. 92/08685 and corresponding to formula (V):

$$HOCH_2—CH(OH)—CH_2—O—[—CH_2—CH(R^{14})—O—]_p—H \quad (V)$$

in which $R^{14}$ represents a linear $C_{14}$ to $C_{18}$ alkyl radical or a group —$CH_2Y$ in which Y is —$OR^{15}$, $R^{15}$ representing a linear $C_{10}$–$C_{18}$, and preferably $C_{16}$, alkyl radical and p represents an average statistical value greater than 1 and not more than 3, and, in addition, when $R^{14}$ is —$CH_2Y$, p can also represent an integer equal to 2; and
(7) fatty acid esters and ethers of α-butylglucoside which either can be mixtures of different fatty acid esters of α-butylglucoside and/or mixtures of different fatty acid ethers of α-butylglucoside, in which the various fatty chains contain a similar number of carbon atoms relative to each other (for example differing by 1 or 2), or can be mixtures of the same fatty acid mono-, di-, tri- or polyesters of α-butylglucoside and/or mixtures of the same fatty acid of mono-, di-, tri- or polyethers of an α-butylglucoside.

The fatty acid esters and ethers of α-butylglucoside used according to the invention preferably contain a fatty chain containing from 8 to 24 carbon atoms, more preferably from 12 to 22 carbon atoms and more particularly from 14 to 18 carbon atoms.

Mention may be made, for example, of lauric ($C_{12}$), myristic ($C_{14}$), palmitic ($C_{16}$), stearic ($C_{18}$) and behenic ($C_{22}$) acid esters and ethers of α-butylglucoside. A mixture of palmitic acid mono- and diester of α-butylglucoside is used more particularly.

The fatty acid esters and ethers of α-butylglucoside in accordance with the invention can be prepared from α-butylglucoside obtained according to the enzymatic manufacturing process described in patent application FR-A-2,680,373, which consists in placing butanol in contact with starch, maltodextrins or maltose in the presence of a purified enzymatic preparation which has α-transglucosylation activity. The fatty acid esters and ethers of α-butylglucoside can be synthesized by reacting the corresponding fatty acid or fatty acid mixture with α-butylglucoside according to standard processes.

The ionic amphiphilic lipids used in combination with the compounds of formula (I) to form the membrane of the vesicles according to the invention can be chosen from:

(1) the following anionic amphiphilic lipids:
natural phospholipids such as egg or soybean lecithin, sphingomyelin, phosphatidylserine, dipalmitoylphosphatidylcholine and hydrogenated lecithins, chemically or enzymatically modified phospholipids and synthetic phospholipids;
the anionic compounds of formula (VI):

in which:
$R^{16}$ represents a $C_7$–$C_{21}$ alkyl or alkenyl radical,
$R^{17}$ represents a saturated or unsaturated $C_7$–$C_{31}$ hydrocarbon-based radical,
M represents H, Na, K, $NH_4$ or a substituted ammonium ion derived from an amine;
anionic compounds such as phosphoric esters of a fatty alcohol, in particular dicetyl phosphate and dimyristyl phosphate in acidic form or in the form of alkaline salts, heptylnonylbenzenesulphonic acid, cholesteryl hydrogen sulphate or cholesteryl hydrogen phosphate, as well as the alkaline salts thereof, lysolecithins, alkyl sulphates such as sodium cetyl sulphate, gangliosides, monosodium and disodium acylglutamates, and in particular the monosodium and disodium salts of N-stearoylglutamic acid, the sodium salts of phosphatidic acid, phosphoaminolipids and natural phospholipids,
(2) the following cationic amphiphilic lipids:
cationic compounds of formula (VII):

in which $R^{18}$ and $R^{19}$, which may be identical or different, represent $C_{12}$–$C_{20}$ alkyl radicals and $R^{20}$ and $R^{21}$, which may be identical or different, represent $C_1$–$C_4$ alkyl radicals,
long-chain amines and the quaternary ammonium derivatives thereof, long-chain amino alcohol esters and the salts and quaternary ammonium derivatives thereof,
polymerizable lipids, as described by Riingsdorf et al. in "Angewandte Chemie", vol. 27, No. 1, January 1988, pages 129–137.

It is possible, in a known manner, to incorporate into the lipid phase constituting the lipid membrane of the vesicles of the invention at least one additive whose main function is to reduce the permeability of the vesicles, to prevent their flocculation and fusion and to increase the degree of encapsulation.

According to a preferred embodiment of the invention, at least one additive preferably chosen from the group formed by:
sterols and in particular phytosterols and cholesterol,
long-chain alcohols and diols,
long-chain amines and the quaternary ammonium derivatives thereof, can be added to the lipid phase.

These additives may optionally have cosmetic and/or dermopharmaceutical activity. This is the case, for example, for cholesterol.

The aqueous continuous phase of the vesicle dispersion according to the invention can consist of water or a mixture of water and at least one water-miscible solvent such as $C_1$–$C_7$ alcohols and $C_2$–$C_5$ alkyl polyols. This aqueous phase can also contain compounds in solution, such as sugars, organic or inorganic salts or polymers. It can also contain a dispersion of droplets of a water-immiscible liquid which the vehicles stabilize, such that it is not necessary to introduce an emulsifier for this stabilization. This immiscible liquid can be chosen from the group formed by animal or plant oils, natural or synthetic essential oils, hydrocarbons, halocarbons, silicones, inorganic acid esters of an alcohol, ethers and polyethers. Examples of water-immiscible liquids are mentioned in patent application EP-A-455,528.

The compositions containing the compounds according to the invention can also contain, in a known manner, one or more active compounds with cosmetic and/or pharmaceutical activity which, depending on their solubility characteristics, can have different localizations. For example, in the case of vesicle dispersions containing an encapsulated aqueous phase, if the active agents are liposoluble, they can be present in the lipid phase constituting the leaflet(s) of the vesicles or in the droplets of water-immiscible liquid stabilized by the vesicles. If the active agents are water-soluble, they can be present in the encapsulated aqueous phase of the vesicles or in the continuous aqueous phase of the dispersion. If the active agents are amphiphilic, they distribute themselves between the lipid phase and the encapsulated aqueous phase with a partition coefficient which varies depending on the nature of the amphiphilic active agent and the respective compositions of the lipid phase and of the encapsulated aqueous phase. In general, the active agents are placed in the lipid phase of the leaflets and/or in the phase encapsulated by the leaflets.

The compositions according to the invention can also comprise, in a known manner, formulation additives which have neither any intrinsic pharmaceutical or cosmetic activity, but which are useful for formulating the compositions. Among these additives, mentioned may be made, for example, of gelling agents, polymers, preserving agents, dyes, opacifiers and fragrances.

The cosmetic or pharmaceutical compositions according to the invention can be, in particular, in the form of shampoos or conditioners, cleansing compositions, skincare or haircare creams, antisun compositions, aftershave creams or mousses, body deodorants, compositions for oral use, hair dye compositions or make-up compositions, for example.

The examples given below, for illustrative purposes and without any limitation at all, will make it possible to gain a better understanding of the invention.

EXAMPLE 1

Preparation of N-octyloxycarbonyl-β-alanyl-L-histidine a) Preparation of N-octyloxycarbonyl-β-alanine 20 g (224.46 mmol) of β-alanine were dissolved in 225 ml of 1N sodium hydroxide solution. 44 ml of octyl chloroformate were then added dropwise, while keeping the pH of the reaction medium above 9 by simultaneous addition of one molar equivalent of 1N sodium hydroxide. After stirring for 6 hours at room temperature, the mixture was acidified with about 1.1 molar equivalents of 3N hydrochloric acid solution. The heterogeneous mixture was extracted with 300 ml of ethyl acetate. The organic phase was washed with 3 times 80 ml of water, dried and then evaporated to dryness. The solid residue was taken up in heptane and then filtered and dried. 51 g of a white product were obtained (yield of 93%).

Melting point: 70–72° C.

Elemental analysis: $C_{12}H_{23}NO_4$, MW=245.3

|  | C | H | N | O |
|---|---|---|---|---|
| Calculated | 58.75 | 9.45 | 5.71 | 26.09 |
| Found | 58.57 | 9.44 | 5.77 | 26.25 |

200 MHz NMR spectrum ($^1H$, DMSO-$d_6$), δ ppm: 12.030 (1H, s, COOH 12), 6.920 (1H, bt, NH 9), 3.750 (2H, t, $CH_2$ 11), 3.010 (2H, m, $CH_2$ 10), 2.210 (2H, t, $CH_2$ 8), 1.090 to 1.360 (12H, m, $CH_2$ 2 to 7), 0.710 (3H, t, $CH_3$ 1).

b) Preparation of N-octyloxycarbonyl-β-alanyl-L-histidine 30 g of N-octyloxycarbonyl-β-alanine were dissolved in 300 ml of dimethylformamide and 1 molar equivalent of triethylamine. Next, 1 molar equivalent of 2-(5-norbornene-2,3-dicarboximido)-1,1,3,3-tetramethyluronium tetrafluoroborate was added. The mixture was then stirred for 1 hour at a temperature of 250° C. Next, a solution containing 1.2 molar equivalents of histidine and 1.2 molar equivalents of sodium hydroxide in 100 ml of water were added dropwise, while keeping the temperature below 30° C. After stirring for 6 hours, the mixture was neutralized with 1 molar equivalent of 5N hydrochloric acid, followed by 100 ml of water. After stirring for 30 minutes, the mixture was poured into 2 liters of acetone. The white precipitate formed was filtered off and dried. The crude product was dissolved in 10 ml/g of refluxing 96% ethanol. The solution was filtered while hot and the product then crystallized at room temperature. After processing the precipitate, 29.4 g of a white crystalline product were obtained (63% yield).

Melting point: 188–190° C.

Elemental analysis: $C_{18}H_{30}N_4O_5 \cdot 2/3H_2O$; MW=394.4

|  | C | H | N | O |
|---|---|---|---|---|
| Calculated | 54.74 | 8.19 | 14.24 | 22.98 |
| Found | 54.75 | 7.94 | 14.19 | 22.96 |

400 MHz NMR spectrum ($^1H$, DMSO-$d_6$), δ ppm: 8.100 (1H, d, NH between 12 and 13), 7.580 (1H, s, CH 17), 6.970 (1H, t, NH between 9 and 10), 6.810 (1H, s, CH 16), 4.400 (1H, m, CH 13), 3.910 (2H, t, $CH_2$ 8), 3.150 (2H, m, $CH_2$ 10), 2.950 (1H, dd, $CH_2$ 14), 2.840 (1H, dd, $CH_2$ 14), 2.270 (2H, t, $CH_2$ 11), 1.510 (2H, m, $CH_2$ 7), 1.250 (10H, m, $CH_2$ 2 to 6), 0.860 (3H, t, $CH_3$ 1).

EXAMPLE 2

Preparation of N-dodecyloxycarbonyl-β-alanyl-L-histidine a) Preparation of N-dodecyloxycarbonyl-β-alanine The compound was prepared according to the same procedure as that in Example 1a) using 55.6 g of dodecyl chloroformate. 27 g of a white product were obtained (yield of 40%).

Melting point: 88–90° C.

Elemental analysis: $C_{16}H_{31}NO_4$; MW=301.43

|  | C | H | N | O |
|---|---|---|---|---|
| Calculated | 63.69 | 10.28 | 4.64 | 21.23 |
| Found | 63.68 | 10.33 | 4.60 | 21.31 |

200 MHz NMR spectrum ($^{13}C$, CDCl$_3$), δ ppm: 177.42 C-16, 156.86 C-13, 65.34 C-12, 36.28 C-14, 34.33 C-15, 31.88 C-11, from 28.92 to 29.61 C-4 to C-10, 25.81 C-3, 22.66 C-2, 14.09 C-1.

b) Preparation of N-dodecyloxycarbonyl-β-alanyl-L-histidine

The compound was prepared according to the same procedure as that in Example 1b), using 30 g of N-dodecyloxycarbonyl-β-alanine. 29.7 g of a white crystalline product were obtained (yield of 68%).

Melting point: 168–172° C.

Elemental analysis: $C_{22}H_{38}N_4O_5$; MW=438.572

|  | C | H | N | O |
|---|---|---|---|---|
| Calculated | 60.25 | 8.73 | 12.77 | 18.24 |
| Found | 59.98 | 8.92 | 12.62 | 17.93 |

400 MHz NMR spectrum ($^1$H, DMSO $d_6$), δ ppm: 8.120 (1H, d, NH 18), 7.590 (1H, s, CH 24), 7.010 (1H, t, NH 14), 6.810 (1H, s, CH 22), 4.400 (1H, m, CH 19), 3.900 (2H, t, $CH_2$ 12), 3.140 (2H, m, $CH_2$ 15), 2.940 (1H, dd, $CH_2$ 20), 2.830 (1H, dd, $CH_2$ 20), 2.260 (2H, t, $CH_2$ 16), 1.510 (2H, m, $CH_2$ 11), 1.260 (18H, m, $CH_2$ 2 to 10), 0.850 (3H, t, $CH_3$ 1).

EXAMPLE 3

Preparation of N-2-ethylhexyloxycarbonyl-α-alanyl-L-histidine hydrochloride 2 g of L-carnosine were dissolved in 10 ml of water and 10 ml of tetrahydrofuran in the presence of 3.5 ml of 10% sodium hydroxide solution. 1.7 g of 2-ethylhexyl chloroformate were added dropwise to the mixture precooled to 10° C. A sodium hydroxide solution was simultaneously introduced in order to keep the pH of the mixture above 9. After 6 hours at room temperature, the mixture was acidified with N/3 hydrochloric acid to a pH equal to 2 and then precipitated from acetone. After filtration and drying, 1.2 g of a white product were obtained (yield of 40%).

Elemental analysis: $C_{18}H_{30}N_4O_5$, HCl; MW=418.7

|  | C | H | N | O | Cl |
|---|---|---|---|---|---|
| Calculated | 51.55 | 7.40 | 13.36 | 19.09 | 8.47 |
| Found | 51.81 | 7.61 | 13.48 | 19.67 | 8.37 |

400 MHz NMR spectrum ($^1$H, DMSO $d_6$+AcOD), δ ppm: 8.830 (1H, d, H 17), 7.280 (1H, s, H 16), 4.550 (1H, m, CH 13), 3.810 (2H, m, $CH_2$ 8), 2.960 to 3.170 (4H, m, $CH_2$ 10 and 14), 2.280 (2H, t, $CH_2$ 11), 1.430 (1H, m, CH 7), 1.190 to 1.290 (8H, m, $CH_2$ 2,3,4,5), 0.760 to 0.810 (6H, 2t, $CH_3$ 1 and 6).

EXAMPLE 4

Comparative Example

The anti-singlet-oxygen activity of the compound of Example 1 was compared with that of N-octanoyl-β-alanyl-L-histidine (referred to as compound A) of the prior art, according to the following principle, which is also described in Pure & Appl. Chem., vol. 62, No. 8, 1467–1476 (1990).

In all the experiments, singlet oxygen was generated by irradiating at 437 nm Ru(bipy)$_3$Cl (tris(2,2'-bipyridyl) ruthenium chloride hexahydrate) dissolved in deuterated methanol.

The sum of the physical inhibition constants ($k_q$) and chemical reaction constants ($k_r$) of singlet oxygen with the test compounds was determined.

The results for the deactivation of singlet oxygen can be analysed by measuring the luminescence (infrared emission) of singlet oxygen at 1270 nm, and by monitoring the kinetics of disappearance of oxygen.

The exploitation of the results is based on the Stern-Volmer type analysis principle: the signal obtained is measured in the absence (So) and in the presence (S) of the test compound, at various concentrations in the solution. The ratio So/S makes it possible to determine the value of $(k_r+k_q)$ according to the following relationship:

$$So/S=\phi_o/\phi=(k_r+k_q)\times\tau_o\times[P]$$

in which relationship:

[P] denotes the concentration of test compound in the solution, $\phi_o$ denotes the quantic yield of the emission in the absence of compound, $\phi$ denotes the quantic yield of the emission in the presence of compound, $\tau_o$ denotes the lifetime of singlet oxygen in deuterated methanol (270 μs), $k_r+k_q$ denotes the sum of the rate constants for the chemical reaction and for the physical inhibition of singlet oxygen.

The following results were obtained:

| Compound | $(k_r + k_q)$ in $1.mol^{-1}.s^{-1}$ |
|---|---|
| Example 1 (invention) | $8.8 \times 10^6 \pm 0.3$ |
| Compound A (not within the invention) | $7.4 \times 10^5 \pm 0.4$ |

The results obtained show that, for the compound according to the invention, the sum of the constants $(k_r+k_q)$ is greater than that for compound A of the prior art: the compound according to the invention (Example 1) thus has significantly higher anti-singlet-oxygen activity than the compound of the prior art (compound A). The compound of Example 1 has higher anti-free-radical activity than compound A.

The method for preparing compound A, N-octanoyl-β-alanyl-L-histidine is described below:

2 g (8.84 mmol) of L-carnosine were dissolved in 10 ml of water and 10 ml of tetrahydrofuran in the presence of 3.5 ml of 10% sodium hydroxide solution. Next, 1.5 ml of capryloyl chloride were added dropwise to the above mixture, cooled to 10° C. After leaving overnight at room temperature, the reaction mixture was precipitated from acetone. The crude product obtained was recrystallized from ethanol. After filtration, washing and drying, 1.8 g of a white product were obtained (yield of 57%).

Elemental analysis: $C_{17}H_{28}N_4O_4$; MW=352.437

|  | C | H | N | O |
|---|---|---|---|---|
| Calculated | 57.94 | 8.01 | 15.9 | 18.16 |
| Found | 57.40 | 7.92 | 15.19 | 18.48 |

500 MHz NMR spectrum ($^1$H, DMSO $d_6$), δ ppm: 8.060 (1H, d, NH 13), 7.700 (1H, t, NH 9), 7.570 (1H, s, H 17), 6.810 (1H, s, H 18), 4.390 (1H, m, CH 14), 3.200 (2H, m, $CH_2$ 10), 2.810 to 2.970 (2H, m, $CH_2$ 15), 2.260 (2H, t, $CH_2$ 11), 2.020 (2H, t, $CH_2$ 7), 1.470 (2H, m, $CH_2$ 6), 1.230 to 1.280 (8H, m, $CH_2$ 2 to 5), 0.860 (3H, t, $CH_3$ 1).

EXAMPLE 5

An oil-in-water emulsion with the composition below was prepared:

| | |
|---|---|
| compound of Example 2 | 0.5 g |
| isostearyl neopentanoate | 10 g |
| triglycerides of caprylic acid and of capric acid | 8 g |
| liquid paraffin | 5 g |
| polyethylene glycol stearate polyglycerolated with 4 mol of ethylene glycol and 2 mol of glycerol, under the name "Hostacerin DGS" by the company Hoechst | 2 g |
| mixture of phosphoric acid ester and oleyl alcohol ether and polyethylene glycol, sold under the name "Crofados N.10 acid" by the company Croda | 4 g |
| glycerol | 4 g |
| glyceryl stearate | 1.3 g |
| thickener | 0.25 g |
| water     qs | 100 g |

A cream which is entirely suitable for daily facial care was thus obtained.

EXAMPLE 6

An oil-in-water emulsion with the composition below was prepared:

| | |
|---|---|
| compound of Example 1 | 1 g |
| octyl palmitate | 12 g |
| polyethylene glycol stearate containing 100 mol of ethylene glycol | 1.3 g |
| glyceryl sorbitan | 0.4 g |
| stearic acid | 1 g |
| thickener | 0.4 g |
| water     qs | 100 g |

A cream for normal skin with a greasy tendency, which applies easily to the face, was thus obtained.

EXAMPLE 7

An oil-in-water emulsion with the composition below was prepared:

| | |
|---|---|
| compound of Example 2 | 1 g |
| octyl octanoate | 10 g |
| dicapryl citrate | 8 g |
| glyceryl stearate | 0.7 g |
| polyethylene glycol (2 mol of ethylene glycol) ether of stearyl alcohol (Brij 72 from ICI) | 0.4 g |
| polyethylene glycol (21 mol of ethylene glycol) ether of stearyl alcohol (Brij 721 from ICI) | 0.8 g |
| polyethylene glycol stearate containing 40 mol of ethylene glycol (Myrj 52 from ICI) | 1.5 g |
| wheat protein hydrolysate | 0.3 g |
| thickener | 0.28 g |
| glycerol | 5 g |
| water     qs | 100 g |

A cream which can be used for daily facial care was thus obtained.

EXAMPLE 8

An oil-in-water emulsion with the composition below was prepared:

| | |
|---|---|
| compound of Example 1 | 0.5 g |
| cyclomethicone | 2 g |
| isostearyl isostearate | 4 g |
| dimethicone copolyol | 2 g |
| stearic acid | 0.5 g |
| water     qs | 100 g |

A white fluid which applies easily to the face was thus obtained.

EXAMPLE 9

A composition in the form of the vesicle dispersion below was prepared:

| | |
|---|---|
| Phase A: | |
| compound of Example 2 | 1.2% |
| cholesterol | 1.8% |
| vitamin E | 0.3% |
| Phase B: | |
| demineralized water | 30% |
| glycerol | 5% |
| lysine | 0.4% |
| Phase C: | |
| distilled water | 15% |
| preserving agents | 0.3% |
| sodium hyaluronate | 0.4% |
| Phase D: | |
| mixture of polycarboxylic acids (Carbopol 980 from the company Goodrich) | 0.20% |
| triethanolamine     qs pH 6.5 | |
| demineralized water     qs | 100% |

The components of phase A were mixed together at 90–110° C. until a homogeneous mixture was obtained. Phase A was introduced with vigorous stirring into phase B, also heated to 90° C. The stirring and the temperature were maintained for 1 hour. The suspension obtained was then treated 3 times with high-pressure homogenization at 600 bar ($6 \times 10^7$ Pa). Vesicles with a particle size of between 100 and 250 nm were thus obtained.

Phase C was then introduced at room temperature, after which phase D was dispersed therein using a deflocculating machine.

A smooth composition which can be used as an anti-ageing care serum is thus obtained.

EXAMPLE 10

A composition in the form of the vesicle dispersion below was prepared:

| | |
|---|---|
| Phase A: | |
| compound of Example 2 | 2% |
| cholesterol | 3% |
| vitamin E | 0.5% |

-continued

Phase B:

| | |
|---|---|
| demineralized water | 35% |
| glycerol | 5% |
| lysine | 0.65% |

Phase C:

| | |
|---|---|
| distilled water | 5% |
| preserving agents | 0.3% |

Phase D:

| | |
|---|---|
| volatile silicone oil | 10% |
| apricot kernel oil | 10% |
| preserving agents | 0.1% |

Phase E:

| | |
|---|---|
| mixture of polycarboxylic acids | 0.20% |
| (Carbopol 980 from the company Goodrich) | |
| triethanolamine    qs pH 6.5 | |
| demineralized water    qs | 100% |

The composition was prepared according to the procedure used in Example 9. Phase D was introduced with vigorous stirring into the vesicle dispersion obtained after incorporating phase C. The mixture was then homogenized twice at 600 bar ($6 \times 10^7$ Pa). The particle size of the oily globules was about 300 nm. Phase E was then dispersed.

A composition which can be used as a day cream for the face is obtained.

EXAMPLE 11

A composition in the form of the vesicle dispersion below was prepared:

Phase A:

| | |
|---|---|
| compound of Example 2 | 1.5% |
| cholesterol | 2.7% |
| vitamin E | 0.8% |
| sorbitan palmitate | 3.8% |

Phase B:

| | |
|---|---|
| demineralized water | 50% |
| glycerol | 5% |
| lysine | 0.5% |

Phase C:

| | |
|---|---|
| distilled water | 5% |
| preserving agents | 0.3% |

Phase D:

| | |
|---|---|
| macadamia oil | 5% |
| preserving agents | 0.3% |

Phase E:

| | |
|---|---|
| mixture of polycarboxylic acids | 0.42% |
| (Carbopol 980 from the company Goodrich) | |
| triethanolamine    qs pH 6.5 | |
| demineralized water    qs | 100% |

The composition was prepared according to the procedure used in Example 10.

A composition which can be used as a day cream for the face is thus obtained.

What is claimed is:

1. A method for combating free radicals comprising adding to said free radicals at least one ingredient chosen from compounds of formula (I) below and acid addition salts thereof:

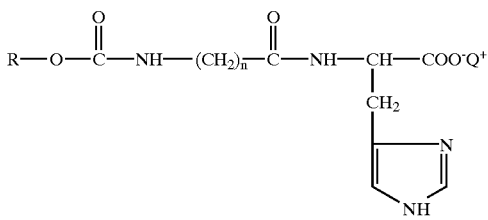

in which:
R is chosen from linear and branched, saturated and unsaturated, alkyl radicals comprising from 6 to 22 carbon atoms,
n is an integer ranging from 1 to 16, and
$Q^+$ is chosen from $H^+$ and organic and inorganic cations.

2. A method for combating free radicals according to claim 1, in which R is chosen from linear and branched, saturated alkyl radicals comprising from 8 to 18 carbon atoms.

3. A method for combating free radicals according to claim 1, in which n is an integer ranging from 1 to 11.

4. A method for combating free radicals according to claim 1, in which said organic cations are chosen from ammoniums containing a residue chosen from basic amino acids and amino alcohols.

5. A method for combating free radicals according to claim 1, in which said inorganic cations are chosen from alkali metal salts, alkaline-earth metal salts and an $NH_4^+$ ion.

6. A method for combating free radicals according to claim 1, in which said acid addition salt is chosen from hydrochlorides, hydrobromides, sulphates, tartrates and acetates.

7. A method for combating free radicals according to claim 1, in which said compounds of formula (I) are chosen from:
N-octyloxycarbonyl-β-alanyl-L-histidine,
N-dodecyloxycarbonyl-β-alanyl-L-histidine,
N-2-ethylhexyloxycarbonyl-β-alanyl-L-histidine hydrochloride, and
N-hexadecyloxycarbonyl-β-alanyl-L-histidine.

8. A method for deactivating singlet oxygen comprising adding to said singlet oxygen at least one ingredient chosen from compounds of formula (I) below and acid addition salts thereof:

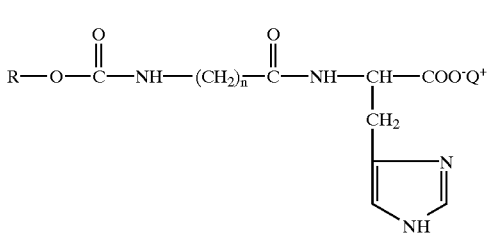

in which:
R is chosen from linear and branched, saturated and unsaturated, alkyl radicals comprising from 6 to 22 carbon atoms,
n is an integer ranging from 1 to 16, and
$Q^+$ is chosen from $H^+$ and organic and inorganic cations.

9. A method for deactivating singlet oxygen according to claim 7, in which R is chosen from linear and branched, saturated alkyl radicals comprising from 8 to 18 carbon atoms.

10. A method for deactivating singlet oxygen according to claim 7, in which n is an integer ranging from 1 to 11.

11. A method for deactivating singlet oxygen according to claim 7, in which said organic cations are chosen from ammoniums containing a residue chosen from basic amino acids and amino alcohols.

12. A method for deactivating singlet oxygen according to claim 7, in which said inorganic cations are chosen from alkali metal salts, alkaline-earth metal salts and an $NH_4^+$ ion.

13. A method for deactivating singlet oxygen according to claim 7, in which said acid addition salt is chosen from hydrochlorides, hydrobromides, sulphates, tartrates and acetates.

14. A method for deactivating singlet oxygen according to claim 7, in which said compounds of formula (I) are chosen from:

N-octyloxycarbonyl-β-alanyl-L-histidine,

N-dodecyloxycarbonylpalanyl-β-alanyl-L-histidine,

N-2-ethylhexyloxycarbonyl-β-alanyl-L-histidine hydrochloride, and

N-hexadecyloxycarbonyl-β-alanyl-L-histidine.

\* \* \* \* \*